(12) United States Patent
Johnson

(10) Patent No.: US 6,406,462 B1
(45) Date of Patent: Jun. 18, 2002

(54) LAP DANCE LINER

(76) Inventor: Wesley Johnson, 1118 W. Magnolia Blvd. #A337, Burbank, CA (US) 91506

( * ) Notice: Subject to any disclaimer, the term of this patent is extended or adjusted under 35 U.S.C. 154(b) by 0 days.

(21) Appl. No.: 09/904,255

(22) Filed: Jul. 11, 2001

(51) Int. Cl.[7] .............................. A61M 1/00; A61F 5/44; A61F 13/15; A41D 27/12; A41B 9/02
(52) U.S. Cl. ........................ 604/327; 604/349; 604/394; 2/54; 2/403
(58) Field of Search .................................. 604/327, 346, 604/347, 349–354, 394; 2/54, 82, 83, 403

(56) References Cited

U.S. PATENT DOCUMENTS

| | | | |
|---|---|---|---|
| 3,366,116 A | * | 1/1968 | Huck |
| 4,601,716 A | | 7/1986 | Smith |
| 4,888,007 A | | 12/1989 | Loeb et al. |
| 4,961,419 A | * | 10/1990 | Tribble et al. |
| 5,163,449 A | | 11/1992 | van der Valk |
| 5,327,911 A | | 7/1994 | Pien |
| 5,531,725 A | | 7/1996 | Steer |
| 5,618,279 A | * | 4/1997 | Pudlo |
| 5,623,946 A | | 4/1997 | Hessel |
| 5,649,913 A | * | 7/1997 | Cohen |
| 5,716,350 A | * | 2/1998 | Ryan |
| 6,007,524 A | * | 12/1999 | Schneider |
| 6,338,729 B1 | * | 1/2002 | Wada et al. |

* cited by examiner

*Primary Examiner*—Dennis Ruhl
(74) *Attorney, Agent, or Firm*—Gene Scott-Patent Law & Venture Group

(57) ABSTRACT

A combination pouch and underwear pant is worn by a man for facilitating sexual activity such as lap dancing. The pouch is worn over the sex organs of a man under the underwear pant, which is adapted by an elastic waistband for compressively pinning the pouch in place. The pouch is made of a flexible and elastic material. A top edge of the pouch provides access to an interior of the pouch of a hand and wrist of the wearer so as to facilitate insertion of the wearer's sex organs into the pouch through an aperture, which encircles penis and scrotum. The aperture elastically compresses between a top surface at the base of the penis of the wearer and a bottom surface at the base of the scrotum of the wearer. With the pouch in place, the wearer is able to facilitate the capture of body fluids without fear of the pouch moving away from its preferred position relative to the torso of the wearer.

7 Claims, 2 Drawing Sheets

LAP DANCE LINER

BACKGROUND OF THE INVENTION

1. Field of the Invention:

This invention relates generally to protective or prophylactic devices for use during sexual activities, and more particularly to a plastic pouch and under-pant combination used for fully clothed sexual activity when penetration is not intended.

2. Description of Related Art:

The following art defines the present state of this field:

Hessel, U.S. Pat. No. 5,623,946, teaches a thin-walled, condom-like tubular protection device for protecting against the transfer of infectious matter during sexual intercourse. The condom-like device has an open end and a collar-shaped outwardly extending portion with an apparatus for radially stretching the collar. The device also has an inner diameter which is sufficiently large to permit movement of a penis with respect to the protective device during coitus.

Steer, U.S. Pat. No. 5,531,725, teaches an improved male incontinence device which has a condom located within a hollow tubular applicator open at both ends, which has an adhesive for securing the device to the penis.

Van der Valk, U.S. Pat. No. 5,163,449, teaches a device for use with a male condom that has a substantially rigid ring with a substantially axial width and a radial thickness. The internal diameter of the device is sized to fit loosely around the base of a penis, adjusting the fit of an ordinary condom and facilitating coitus.

Loeb, et al., U.S. Pat. No. 4,888,007, teaches a pubic shield which has a resilient tubular element and which is secured to the user with a bio-adhesive. The shield is designed for use with a condom.

Smith, U.S. Pat. No. 4,601,716, discloses a disposable sanitary sheath for wearing around the penis of the user. The sheath contains a moisture absorbent pad and is surrounded with an outer moisture resistant layer.

Pien, U.S. Pat. No. 5,327,911, discloses a universal contraceptive device having a condom support device of annular configuration and including an inwardly opening groove formed on the periphery thereof. A securing device secures the support device in place on a person's body, and the support device holds a condom which fits loosely around an erect male organ.

The prior art teaches various condom or other sheathing devices to fit over a man's penis to protect the user from disease transmission and to contain body fluids. However, the prior art does not teach a pouch and underpant combination designed specifically for providing frictional stimulation to the penis during fully clothed sexual activity. The present invention fulfills these needs and provides further related advantages as described in the following summary.

SUMMARY OF THE INVENTION

The present invention teaches certain benefits in construction and use which give rise to the objectives described below.

A combination pouch and underwear pant is worn by a man for facilitating sexual activity such as lap dancing. The pouch is worn over the sex organs of a man and under the underwear pant, which is adapted by an elastic waistband for compressively pinning the pouch in place. The pouch is made of a flexible and elastic material with a rough interior surface. A top edge of the pouch provides access to an interior of the pouch of a hand and wrist of the wearer so as to facilitate insertion of the wearer's sex organs into the pouch through an aperture which encircles penis and scrotum compressively. The aperture elastically compresses between a top surface at the base of the penis of the wearer and a bottom surface at the base of the scrotum of the wearer so that the pouch is held in place during use. With the pouch in place, the motion of a lap dancer against the outer clothes of the wearer is able to cause the roughened surface of the pouch to slide against the penis in such a manner that the penis is stimulated so as to simulate intercourse. The pouch captures fluids released prior to, and during the lap dance act.

A primary objective of the present invention is to provide a lubricated, loose fitting liner, which covers a user's genitals during sexual activity, the device having advantages not taught by the prior art.

Another objective is to provide a liner device, which is held in place by an underwear pant, thus eliminating the need for any further attachment devices, or requiring the liner device to clamp or adhere to any part of the user's torso.

A further objective is to provide a device enabled for capturing body fluids, such as ejaculate, protecting the user's clothes and facilitating cleanup after sexual activity.

Another objective is to provide a liner device, which is lubricated and rough surfaced to enhance physical pleasure when the user's genitals are manipulated and to allow motion to cause sliding stimulation against the genital area.

A final objective is to provide a device as described which is not noticeable when worn.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings.

DETAILED DESCRIPTION OF THE INVENTION

Figure 1:
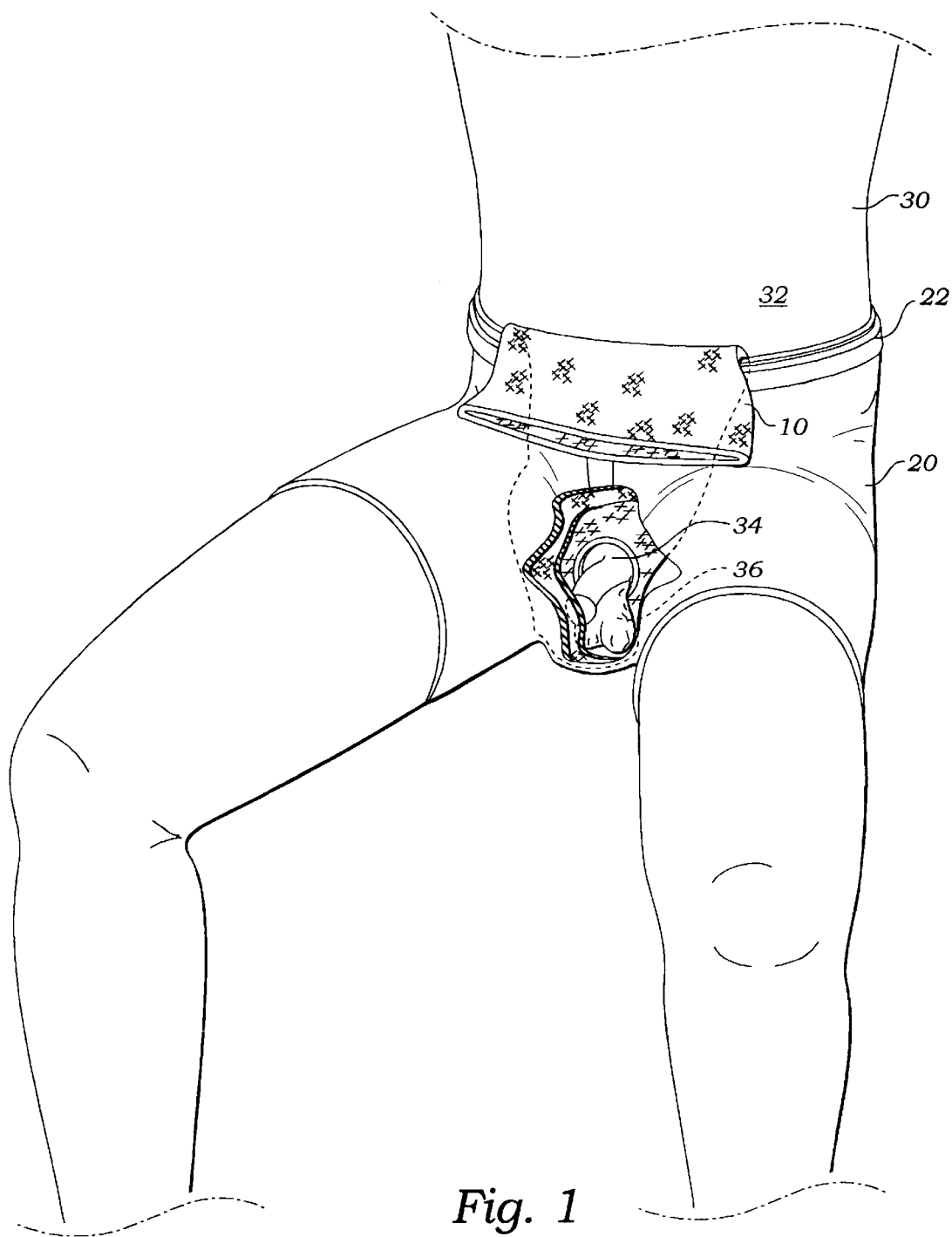
FIG. 1 is a cutaway perspective view showing the front panels of a pouch and pant combination of the preferred embodiment of the present invention, the pant being cutaway to reveal the pouch within, a front panel of the pouch cutaway to reveal the sex organs of a man positioned within the pouch through an aperture on a rear panel of the pouch.

The above described drawing figures illustrate the preferred embodiment of the invention, a combination pouch 10 and underwear pant 20 worn by a man 30 for facilitating sexual activity when the intention is to perform such activity while fully clothed and when sexual penetration is not intended.

The underwear pant 20 is a common article of clothing well known in the art and provides a tight fitting elastic waistband 22 for compressively encircling a torso 32 of a wearer, normally a man. The waistband 22 may also be of the type that is drawn and tied, or other types that may provide similar function, all of which is well known.

Figure 2:
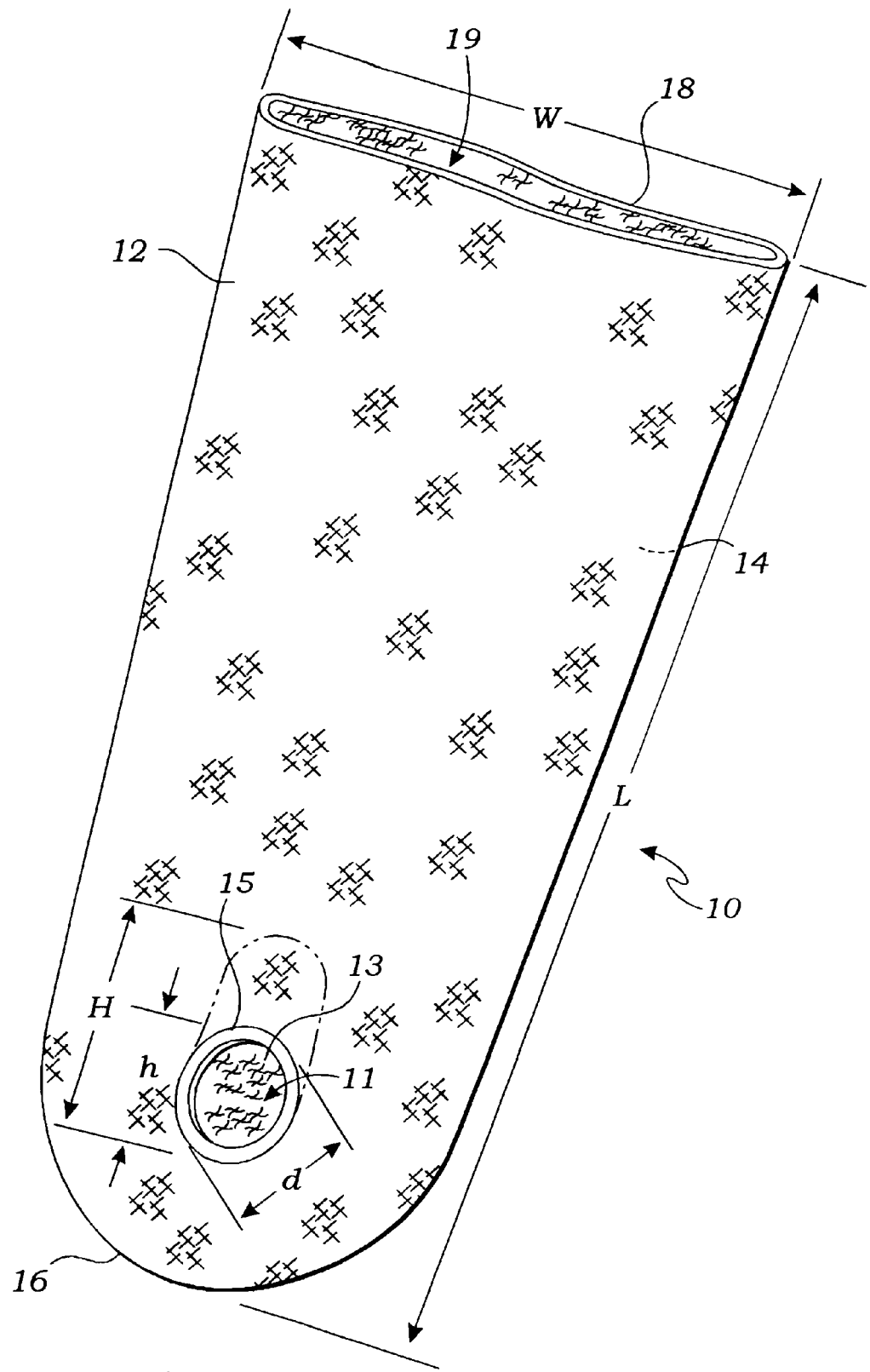
FIG. 2 is a perspective view of the pouch thereof showing the rear panel.

The pouch 10 is of a type that is not known, and comprises features that enable a new and valuable use. The pouch 10 and pant 20, when used together in the manner described and shown, provides a combination that is not known in the art. The pouch 10 is generally rectangular in shape, as shown in FIG. 2, and is made of a flexible and elastic material such as a rubberized plastic combination or similar materials. The pouch is folded to provide a front panel 14 and a rear panel 12. A top edge 18 of the pouch is open, providing access to an interior 19 of the pouch by a hand and wrist of the wearer. The rear panel 12 of the pouch provides an aperture 11, enabled by its size for admitting the penis and scrotum of the wearer into the pouch 10 as is illustrated in FIG. 1. This aperture 11 is adapted by size and the elastic property of the pouch 10 for compressive engagement between a top surface 34 at the base of a penis of the wearer and a bottom surface 36 at the base of a scrotum of the wearer. This aspect of the invention is critical to its use. Being elastic and flexible, and preferably lubricated, the pouch 10 would be normally easily dislodged from its preferred engagement with the sex organs of the wearer, as shown in FIG. 1 because of the vigorous activity the sex organs and pouch 10 are subjected to during use. However, it has been found that with a moderate elastic compressive force around the penis and scrotum, the pouch 10 is more permanently fixed in place and is therefore not easily dislodged. A further important feature of the pouch 10 is that it is of such length, see "L" in FIG. 2, as to extend upwardly and under the waistband 22 of the pant 20. This enablement allows the pant waistband 22 to control the position of the pouch essentially pinning it in place during use. The pouch is at least 2½ inches in width and preferably larger so as to admit the hand and wrist to the interior 19 of the pouch 10. An important feature of the pouch 10 is that the interior sidewall surface 13 has a roughness of at least ½ mm in height. This roughness is necessary for appropriate stimulation to the male sex organ for stimulation thereof and is a critical element in the novelty of the invention. The pouch is approximately 13 inches in length; dimension "L." The aperture is at least 1 inch in diameter; dimension "d." These dimensions have been found to be critical to the proper fitting of the invention to the average male. A lubricating layer, such as a layer of Vaseline® is deposited on the interior sidewall surface 13 adjacent the male organ. A reinforcing grommet 15, such as a reinforcing circular portion, as shown, is preferably placed integral with the sidewall 12 of the pouch around the aperture 11 and has been found to be critical to the ability of providing proper elastic force for holding the pouch 10 in place, i.e., sufficient elastic force, while enabling the material of the pouch 10 to be sufficiently thin to enable the pouch to slide and respond to pressures during lap dancing. In FIG. 2, the dimension "h" represents the relaxed length or size of the aperture 11, while the dimension "H" represents the extended length or size of the aperture 11 when it is pulled to stretch around the penis and scrotum. The material of the pouch 10 including the grommet 15 is of sufficient elastic property for encompassing a range of male size sufficient to the intended market of users. It is the ability of the material that the pouch 10 is made of to stretch elastically to provide the holding power necessary during use.

In use, the pouch 10 is placed into the pant 20 and, with a hand and arm inserted into the pouch, the aperture 11 is manually stretched to receive the sex organs of the wearer into the pouch 10. If the pouch 10 is not pre-lubricated, a lubricant is applied to the interior surface 13 of the pouch 10 around the sex organs. The upper portion of the pouch is drawn upward with the top edge 18 pinned in place by the pant 20. The wearer normally wears a trousers and shirt over the invention. During sexual play well known as "lap dancing" the wearer receives friction from a lap dancing person with direct physical contact onto the sexual organs of the wearer. During this play body fluids may be released by the wearer, and these fluids are captured within the pouch 10. The tight fit of the stretched aperture and the elastic band 22 prevent these fluids from leaving the interior 19 of the pouch 10.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A combination liner device and underwear pant worn by a man for facilitating sexual activity, the combination comprising: an underwear pant adapted by a tight fitting waistband for compressively encircling a torso of a wearer; and, positioned within the underwear pant, a generally rectangular pouch of a flexible and elastic material, the pouch having a front and a rear panels and a top edge providing access to an interior of the pouch by a hand and wrist of the wearer; the rear panel of the pouch providing an aperture enabled by size for admitting a penis and scrotum of the wearer into the pouch, and adapted by size and elastic property for elastic compressive engagement between a top surface of a base of a penis of the wearer and a bottom surface of a base of a scrotum of the wearer; the pouch adapted by length for extending under the elastic waistband for securing the pouch in a preferred position.

2. The combination of claim 1 wherein the pouch is at least 2½ inches in width.

3. The combination of claim 1 wherein the front and rear panels provide an interior surface having a roughness of at least ½ mm in height.

4. The combination of claim 1 wherein the pouch is approximately 13 inches in length.

5. The combination of claim 1 wherein the aperture is at least 1 inch in diameter.

6. The combination of claim 3 further comprising a lubricating layer on the interior surface.

7. The combination of claim 1 further comprising a reinforcing grommet around the aperture.

* * * * *